United States Patent
Cheskis et al.

(10) Patent No.: US 10,358,415 B2
(45) Date of Patent: Jul. 23, 2019

(54) PROCESSES FOR THE PREPARATION OF UNSATURATED MALONATES

(71) Applicant: International Flavors & Fragrances Inc., New York, NY (US)

(72) Inventors: Michael Cheskis, Nesher (IL); Yigal Becker, Tel-Aviv (IL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 15/556,689

(22) PCT Filed: Mar. 11, 2016

(86) PCT No.: PCT/US2016/021949
§ 371 (c)(1),
(2) Date: Sep. 8, 2017

(87) PCT Pub. No.: WO2016/145288
PCT Pub. Date: Sep. 15, 2016

(65) Prior Publication Data
US 2018/0105490 A1 Apr. 19, 2018

Related U.S. Application Data

(60) Provisional application No. 62/131,647, filed on Mar. 11, 2015.

(51) Int. Cl.
*C07C 403/20* (2006.01)

(52) U.S. Cl.
CPC ........ *C07C 403/20* (2013.01); *C07C 2601/16* (2017.05)

(58) Field of Classification Search
CPC .......................... C07C 403/20; C07C 2601/16
USPC ....................................................... 562/509
See application file for complete search history.

(56) References Cited

U.S. PATENT DOCUMENTS

| | | | |
|---|---|---|---|
| 7,932,418 B2 | 4/2011 | Mimoun et al. | |
| 8,765,980 B2 | 7/2014 | Schroder et al. | |
| 9,216,935 B2 | 12/2015 | Tadepalli et al. | |
| 2012/0083488 A1* | 4/2012 | Kinoshita | C07D 209/56 |
| | | | 514/217.03 |

FOREIGN PATENT DOCUMENTS

| | | |
|---|---|---|
| EP | 2513030 B2 | 8/2018 |
| WO | 2006010287 A1 | 2/2006 |
| WO | 2012085056 A1 | 6/2012 |

OTHER PUBLICATIONS

Ranu et al., Ionic Liquid as Catalyst and Reaction Medium—A Simple, Efficient and Green Procedure for Knoevenagel Condensation of Aliphatic and Aromatic Carbonyl Compounds Using a Task-Specific Basic Ionic Liquid, European Journal of Organic Chemistry, vol. 2006. (Year: 2006).*
Van den Brand et al., "Acid-Base Characterization of Aluminum Oxide Surfaces with XPS", Journal of Physical Chemistry B, vol. 108, 2004, pp. 6017-6024. (Year: 2004).*
Clay, R.J., T.A. Collom, G.L. Karrick and J. Wemple (Mar. 1993) "A Safe, Economical Method for the Preparation of 3-Oxo Esters." Synthesis 290-292.
Hashiguchi, S., H. Natsugari and M. Ochiai (1988) "Synthesis of g-Lactam Analogues of Carbapenems with Substituted-thio Groups at the C-3 Position." J. Chem. Soc. Perkin Trans. 1:2345-2352.
Krapcho, A.P. (1982) "Synthetic Applications of Dealkoxycarbonylations of Malonate Esters, B-Keto Esters, a-Cyano Esters and Related Compounds in Dipolar Aprotic Media—Part I." Synthesis 805-822.
Ogiwara, Y., K. Takahashi, T. Kitazawa and N. Sakai (2015) "indium(III)-Catalyzed Knoevenagel Condensation of Aldehydes and Activated Methylenes Using Acetic Anhydride as a Promoter." J. Org. Chem. 80:3101-3110.
Texier-Boullet, F and A. Foucaud (1982) "Knoevenagel Condensation Catalyzed by Aluminium Oxide." Tetrahedron Letters 23:4927-4928.
Extended European Search Report and Written Opinion dated Sep. 11, 2018 from EP 16762578.9, filed Mar. 11, 2016.
International Search Report and Written Opinion in PCT/US16/21949 dated Jun. 3, 2016.
International Preliminary Report on Patentability in PCT/US16/21949 dated Sep. 12, 2017.

* cited by examiner

*Primary Examiner* — Deborah D Carr
(74) *Attorney, Agent, or Firm* — Martin Zhang; Xufan Tseng; Elizabeth M. Stover

(57) ABSTRACT

Disclosed is a process for preparing unsaturated malonates and/or their isomers. The process includes the step of reacting an aldehyde and a dialkyl malonate in the presence of a Lewis acid and a carboxylic acid thereby forming an unsaturated malonate.

20 Claims, No Drawings

PROCESSES FOR THE PREPARATION OF UNSATURATED MALONATES

CROSS REFERENCE TO RELATED APPLICATIONS

This application is a national stage entry under 35 USC 371 for International Application No. PCT/US2016/021949, filed on Mar. 11, 2016 . The international application claims priority to US Provisional Application No. 62/131,647, filed on Mar. 11, 2015 . The contents of both applications are incorporate by reference in their entirety.

TECHNOLOGICAL FIELD

The present application provides processes for the preparation of unsaturated malonates with shortened reaction time and improved yields.

BACKGROUND

Unsaturated dialkyl esters such as Compound (I) are conveniently prepared by Knoevenagel condensation of aldehydes (e.g., 2-Methyl-4-(2,6,6-trimethylcyclohex-1-en-1-yl)butanal, Compound III) with dialkyl malonates such as dimethyl or diethyl malonate.

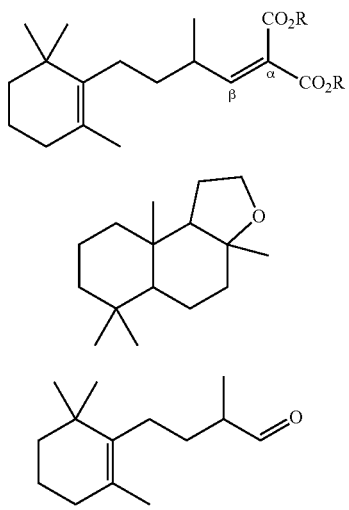

The Knoevenagel condensation of aldehydes with dialkyl malonates is traditionally carried out in boiling toluene as solvent in presence of catalytically effective amounts of piperidinium acetate. Water formed in the reaction is continuously separated as an azeotrope. See G. Jones in "Organic Reactions" Vol. 15, J. Wiley, 1967). Long reaction times and low to moderate yields are obtained when these conditions are applied on Compound III. Under this conventional Knoevenagel condensation condition, the reaction suffers a long reaction time and a low yield.

Lehnert reported an improvement to the yield of the conventional Knoevenagel condensation by carrying out the condensation in presence of two equivalents of titanium tetrachloride and four equivalents of pyridine in tetrahydrofuran at 0-25° C. However, the reaction time was prolonged. See Lehnert et al., Tetrahedron Letters 54, 4723-24 (1970). Indeed, when Lehnert conditions were used to prepare the dialkyl ester Compound I from the aldehyde Compound III, the reaction gave a yield of 81% with a reaction time of 18 hours at 25° C. See U.S. Pat. No. 8,765,980. In addition to the prolonged reaction time, the Lehnert improvement has another disadvantage, namely, the use of a large amount of titanium tetrachloride, an environmental and health hazard. Titanium tetrachloride explosively reacts with water, forming solid waste titanium dioxide and corrosive gas hydrogen chloride.

There is still a need for a green process for preparing unsaturated dialkyl esters with a high yield and a short reaction time, and without recourse to excessive amounts of corrosive and toxic chemical reagents.

SUMMARY OF THE INVENTION

This invention is based on a green process for preparing $\alpha,\beta$-unsaturated dialkyl malonates, which, unexpectedly, has a high yield and a short reaction time.

Accordingly, one aspect of the invention relates to a process for the preparation of unsaturated malonates, or any isomers (including stereoisomers) thereof, comprising the step of:

performing a reaction between an aldehyde of formula A with a dialkyl malonate of formula B

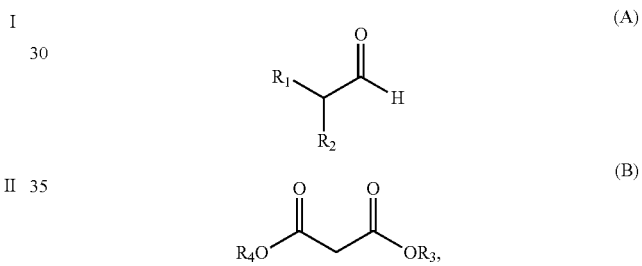

wherein each of $R_1$, $R_2$, $R_3$ and $R_4$ is, independently, a straight or branched $C_1$-$C_{20}$ alkyl, straight or branched $C_2$-$C_{20}$ alkenyl, or straight or branched $C_2$-$C_{20}$ alkynyl.

The reaction is carried out in the presence of a Lewis acid and a carboxylic acid, and, optionally, an aprotic dipolar solvent. The product of the reaction contains an unsaturated malonate of formula C:

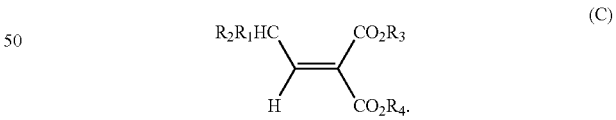

The molar ratio between the aldehyde of formula A and the dialkyl malonate of formula B is 1:10 to 2:1 (e.g., 1:5 to 1:1 and 1:2 to 1:1).

Suitable Lewis acids include compounds of formula $MX_n$, wherein M is a metal selected from group IA (alkali metals) or IIA (alkaline earth metals) in the periodic table; X is a halogen (e.g., F, Cl, Br, and I); and n is 1-4 (e.g., 1, 2, 3, or 4). One or more Lewis acids can be used in the reaction.

In some embodiments, the carboxylic acid is selected from the group consisting of formic acid, acetic acid, propionic acid, citric acid, and any combinations thereof.

In other embodiments, the aprotic dipolar solvent is selected from the group consisting of N,N-dimethylformamide (DMF), N,N-dimethylacetamide (DMAC), N-Methyl-2-pyrrolidone (NMP), dimethylsulfoxide (DMSO), and any combinations thereof.

In certain embodiments, the process of the invention is conducted at a temperature in the range of 100° C. to 160° C. for 5 hours or less (e.g., 3 hours or less, 0.1 hours to 5 hours, 0.2 to 3 hours, and 0.5 to 2 hours).

The process of the invention can further produce at least one compound of formula (D), one compound of formula (E), one compound of formula (F), or any isomer (including stereoisomer) thereof:

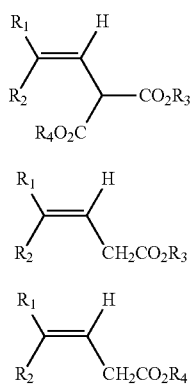

wherein $R_1$, $R_2$, $R_3$ and $R_4$ are as defined herein above.

In other embodiments, the process forms a product containing a mixture of a compound of formula (C), a compound of formula (D), a compound of formula (E), and a compound of formula (F).

In another embodiment, the process of the invention further comprises the step of converting a compound of formula (C) or (D) under an alkoxydecarbonylating condition thereby forming a compound of formula (E) or (F), or any isomer (including stereoisomer) thereof.

The term "alkyl," as used herein, means a linear or branched saturated hydrocarbon group containing from 1 to 20 carbon atoms, preferably 1 to 12 carbon atoms, sometimes more preferably 1 to 6 carbon atoms ("lower alkyl"), and sometimes more preferably 1 to 4 carbon atoms, which is connected with the rest of the molecular moiety through one or more single bonds. Representative examples of alkyl include, but are not limited to, methyl ("Me"), methylene (i.e., a bivalent methyl), ethyl ("Et"), ethylene, n-propyl, n-propylene, iso-propyl, iso-propylene, n-butyl, sec-butyl, iso-butyl, tent-butyl, n-butylene, sec-butylene, iso-butylene, tert-butylene, etc.

The term "alkenyl" refers to a linear or branched hydrocarbon group of 1 to 20 (e.g., 2-10 and 2-6) carbon atoms and one or more double bonds. Examples include —CH═CH$_2$, —CH═CHCH$_3$, —CH$_2$CH═CH$_2$, and —CH$_2$CH═CHCH$_3$.

The term "alkynyl" refers to a linear or branched hydrocarbon group of 1 to 20 (e.g., 2-10 and 2-6) carbon atoms and one or more triple bonds.

The term "halo" or "halogen" refers to F, Cl, Br, and I, preferably Cl, Br, and I.

Each of the alkyl, alkenyl, and alkynyl can be substituted with aryl, heteroaryl, cycloalkyl, cycloheteroalkyl, or halo. An exemplary alkyl is 2-(2,6,6-trimethylcyclo-1-en-1-yl) ethyl.

The term "aryl," as used herein, means an aromatic hydrocarbon group having 6 to 14, preferably 6 to 10, carbon atoms formed from an aromatic hydrocarbon by loss of a hydrogen atom. Representative examples of aryl include, but are not limited to, phenyl and naphthyl.

"Heteroaryl" means a monocyclic or fused bicyclic group of 5 to 12 ring atoms containing one or more, preferably one, two, three, or four ring heteroatoms independently selected from the group of N, O, P(O)$_m$, —Si (where Si is substituted with alkyl and one additional group selected from alkyl, alkenyl, cycloalkyl-alkyl, aryl, aralkyl, heteroaralkyl, and optionally substituted heterocycloalkylalkyl), and S(O)$_n$, where m is 1 or 2 and n is 0, 1, or 2, the remaining ring atoms being carbon, wherein the ring comprising a monocyclic radical is aromatic and wherein at least one of the fused rings comprising a bicyclic radical is aromatic. One or two ring carbon atoms can optionally be replaced by a —C(O)—, —C(S)—, or C(═NH)— group. Unless otherwise stated, the valency may be located on any atom of any ring of the heteroaryl group, valency rules permitting. More specifically, the term heteroaryl includes, but is not limited to, phthalimidyl, pyridinyl, pyrrolyl, pyrazolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), pyrazinyl, pyrimidinyl, pyridazinyl, oxazolyl, isoxazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, methylenedioxyphenyl (including, for example, methylenedioxyphen-5-yl), and the derivatives thereof, or N-oxide or a protected derivative thereof. The heteroaryl ring is unsubstituted or may be substituted with one, two, or three "ring system substituents" which may be the same or different, and are as defined herein.

The term "cycloalkyl," as used herein, means a cyclic hydrocarbon group containing from 3 to 8 carbon atoms, preferably 3 to 6 carbon atoms, where such groups can be saturated or unsaturated, but not aromatic. In certain embodiments, cycloalkyl groups are preferably fully saturated, or have one or two C═C double bonds. Examples of cycloalkyl include, but are not limited to, cyclopropyl, cyclobutyl, cyclopentyl, cyclohexyl, cyclohexenyl, etc.

"Heterocycloalkyl" means a saturated or unsaturated, nonaromatic, 5-8 membered monocyclic, 8-12 membered bicyclic, or 11-14 membered tricyclic ring system having one or more heteroatoms (e.g., O, N, P, and S). Examples include 3-piperidonyl, 4-piperidonyl, 5-piperidinonyl, 6-piperidinonyl, piperidinyl, piperazinyl, imidazolidinyl, imidazolidonyl, azepanyl, pyrrolidinyl, 2-pyrrolidonyl, 3-pyrrolidonyl, dihydrothiadiazolyl, dioxanyl, morpholinyl, 2-morpholinonyl, 3-morpholinonyl, tetra-hydropuranyl, and tetrahydrofuranyl. The term "heterocyclo-alkylene" refers to bivalent heterocycloalkyl.

Each of aryl, heteroaryl, cycloalkyl, and cycloheteroalkyl can be substituted with alkyl, alkenyl, alkynyl, aryl, heteroaryl, cycloalkyl, cycloheteroalkyl, and halo.

The singular forms "a", "an", and "the" include plural references, and vice versa, unless the context clearly dictates otherwise.

The values and dimensions disclosed herein are not to be understood as being strictly limited to the exact numerical values recited. Instead, unless otherwise specified, each such value is intended to mean both the recited value and a functionally equivalent range surrounding that value. For example, a value disclosed as "50%" is intended to mean "about 50%."

The details of one or more embodiments of the invention are set forth in the description below. Other features, objects, and advantages of the invention will be apparent from the description and the claims.

DETAILED DESCRIPTION

Dialkyl malonates (e.g., dialkyl 2-(2-methyl-4-(2,6,6-trimethylcyclohex-1-enyl)butylidene)malonates, Compound I as shown below) are intermediates for preparing commercially important compounds such as fragrance ingredient 3a,6,6,9a-tetramethyldodecahydronaphtho[2,1-b]furan (Compound II shown below), which has a strong ambergris odor. Compound II is commercially available as Cetalox® (Firmenich S.A.), Cetalor (Aromor Flavors & Fragrances), Ambroxan® (Kao) and Ambermor (Aromor).

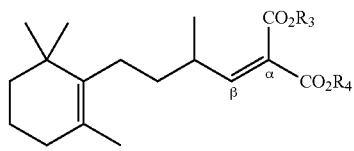

I

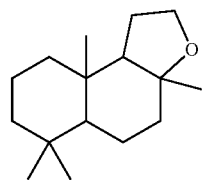

II

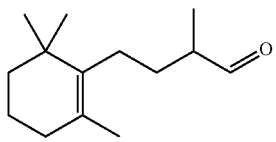

III

To prepare Compound II, the unsaturated malonate Compound I is first transformed via alkoxydecarbonylation (Synthesis, 805-822, 1982) to alkyl 4-methyl-6-(2,6,6-trimethyl-cyclohex-1-enyl)hex-3-enoate (Compound IV shown below), which is then converted to Compound II. See WO 2006/010287, and U.S. Pat. Nos. 8,765,980 and 7,932,418.

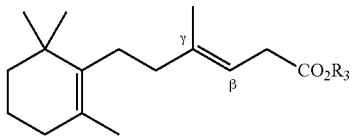

IV

It has been found that that α,β-unsaturated alkyl malonates, such as dialkyl 2-(2-methyl-4-(2,6,6-trimethyl-cyclohex-1-enyl) butylidene) malonates (Compound I) can be prepared by condensing the corresponding aldehydes, such as 2-Methyl-4-(2,6,6-trimethylcyclohex-1-en-1-yl)butanal (Compound III) with dialkyl malonates of the formula $CO_2R_3CH_2CO_2R_4$ where each of $R_3$ and $R_4$, independently, is a straight or branched $C_1$-$C_8$ alkyl. The condensation reaction is typically carried out in the presence of a catalytic amount of a Lewis acid and a carboxylic acid, optionally in an aprotic dipolar solvent.

In some embodiments, the Lewis acid is $MX_n$, wherein M is an alkali or alkaline metal selected from Groups IA (i.e., Li, Na, K, Rb, Cs, and Fr) and IIA (Be, Mg, Ca, Sr, Ba, and Ra) in the periodic table, and X is a halogen (i.e., F, Cl, Br, and I). In certain embodiments, the Lewis acid is selected from the group consisting of lithium iodide, lithium bromide, lithium chloride, magnesium iodide, magnesium bromide and magnesium chloride. In other embodiments, the Lewis acid is magnesium chloride. In specific embodiments, magnesium chloride is used at a level of 0.1 to 3 (e.g., 0.2 to 2, 0.4 to 1, 0.5 to 1, 0.5 to 0.8, and 0.75) equivalents based on the aldehyde of formula A.

Surprisingly, it was found that the reaction is accelerated by addition of a catalytically effective amount of a carboxylic acid of formula $RCO_2H$ where R is selected from the group consisting of H, straight or branched $C_1$-$C_8$ alkyl, and $C_5$-$C_8$ aryl.

Preferably, the carboxylic acid is formic acid, acetic acid, propionic acid, citric acid, or a combination thereof. More preferably, the carboxylic acid is formic acid. In some embodiments, the carboxylic acid is used at a level of 0.1 to 1 equivalents (e.g., 0.2 to 0.3 equivalents) based on the aldehyde of formula A. It is to be noted that without adding the carboxylic acid, the reaction requires a significantly longer reaction time.

In some embodiments, the reaction between the compound of formula A and the compound of formula B is carried out at a temperature of 50 to 200° C. (e.g., 100 to 160° C., 110 to 150° C., 125 to 135° C., and 130° C.).

In addition to the product of an α,β-unsaturated malonate, such as Compound I, the process of the invention may also produce one or more additional products, such as an (E or Z)-β,γ-unsaturated malonate (e.g., (E or Z)-dialkyl 2-(2-methyl-4-(2,6,6-trimethyl-cyclohex-1-en-1-yl)butylidene) malonate as Compound V), a β,γ-unsaturated alkyl ester (e.g., Compound IV), and/or an α,β-unsaturated monoester (e.g., Compound VI). Compound VI is a byproduct not suitable for preparing the final fragrance ingredient, Compound II. Although, in theory, an elevated temperature (such as 100 to 200° C.) favors the formation of the undesired compound VI, the inventors have found that the addition of the carboxylic acid (e.g., anhydrous formic acid) substantially suppresses the formation of the undesired by product Compound VI.

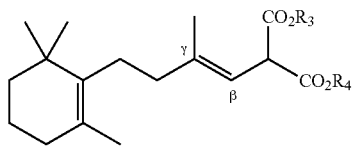

V

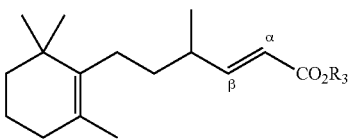

VI

The (E or Z)-β,γ-unsaturated isomer such as Compound V is also a useful intermediate for preparing β,γ-unsaturated alkyl esters, such as alkyl (E or Z)-4-methyl-6-(2,6,6-trimethylcyclohex-1-en-1-yl)hex-3-enoate (Compound IV) since the mixture of α,β-unsaturated alkyl malonates, such as Compound I, and (E or Z)-β,γ-unsaturated alkyl diesters, such as Compound V is converted to β,γ-unsaturated alkyl esters at elevated temperatures (in some embodiments in the range of 160 to 180° C.) via an alkoxydecarbonylating condition. Alternatively, such reactions can be performed by trans-esterification techniques as well.

The process of this invention can occur either in a batch reactor, a semicontinuous reactor, or a continuous reactor.

A batch reactor refers to a conventional static reactor, in which the aldehyde of formula A, the dialkyl malonate of formula B, the Lewis acid, the carboxylic acid, and the aprotic dipolar solvent are secured in the reactor to allow the Knoevenagel condensation reaction to occur.

A semicontinuous or continuous reactor refers to a flow reactor including a single Continuous Stirred Tank Reactor (CSTR), multiple CSTRs in series, or a microreactor. See U.S. Pat. No. 9,216,935.

In some embodiments, a solution of the starting materials (e.g., the aldehyde, malonate, Lewis acid, and carboxylic acid) is pumped into a flow reactor. In other embodiments, the starting materials are separately dissolved in a solvent. Their solutions are mixed in-line using a static mixer before entering the reactor. In still other embodiments, the reactor may be packed with materials such as a Lewis acid and glass beads (10 to 100 μm particle size).

As used herein, the terms "packed" and "packing" mean to fill with an amount of materials that allow effective production of the product and the amount of the packing materials often requires taking into consideration, e.g., the size of the reactor vessel, the material type, the reaction temperature, the ratio among the products (if multiple products exist), and the yields of the products.

In some embodiments, the reactor system is heated using a heating circulating oil bath or electrical heater. From the reactor system, the reaction mixture is collected in a product receiver. The reaction mixture is analyzed for reaction completion using an instrument such as Gas Chromatography (GC).

All parts, percentages and proportions referred to herein and in the claims are by weight unless otherwise indicated.

As used herein L is understood to be liter, mL is understood to be milliliter, M is understood to be mole/liter, μm is understood to be micrometer, nm is understood to be nanometer, mol is understood to be moles, mmol is understood to be millimole, g is understood to be gram, kg is understood to be kilogram, and min is understood to be minutes.

The invention is described in greater detail by the following non-limiting examples. Without further elaboration, it is believed that one skilled in the art can, based on the description herein, utilize the present invention to its fullest extent without undue experimentation.

All publications cited herein are incorporated by reference in their entirety.

EXAMPLE 1

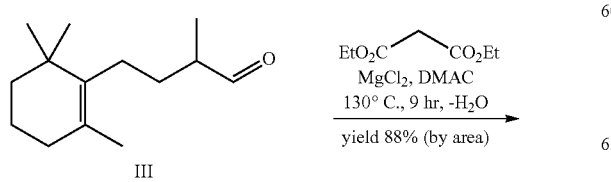

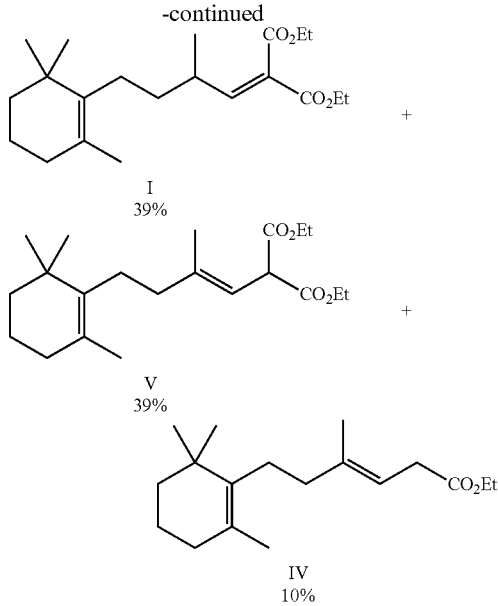

In a flask, 2-methyl-4-(2,6,6-trimethylcyclohex-1-en-1-yl)butanal (Compound III, 2 g, 9 mmol, 96% purity), diethyl malonate (2.2 g, 13.7 mmol), N,N-dimethyl-acetamide ("DMAC," 2.4 g) and MgCl$_2$ (0.59 g, 6.2 mmol) were stirred at 130° C. for 9 hours. According to gas chromatographic (GC) analysis, the reaction mixture contained 39% α,β-diester Compound I, 39% (E)-β-γ-diester Compound V, 10% (E)-β-γ-ester Compound IV, and 1.5% unreacted Compound III.

EXAMPLE 2

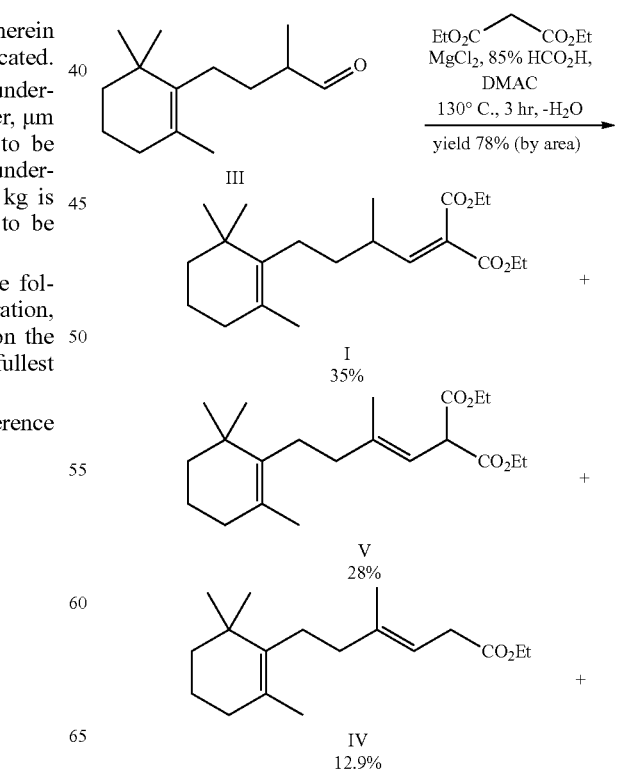

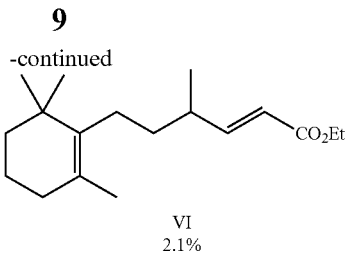

VI
2.1%

Formic acid (85%, 0.65 g, 12 mmol) was added to a mixture of 2-methyl-4-(2,6,6-trimethylcyclohex-1-en-1-yl) butanal (Compound III, 2 g, 9 mmol, 96% purity), N,N-dimethyl-acetamide (2.5 g), diethyl malonate (2.2 g, 13.6 mmol) and MgCl$_2$ (0.7 g, 7.4 mmol). The reaction mixture was stirred for 3 hours at 130° C. Compound III was completely consumed. According to GC analysis, the reaction mixture contained 35% α,β-diester Compound I, 28% (E)-β-γ-isomer Compound V, 12.9% (E)-β-γ-ester Compound IV, and 2.1% α,β-ester Compound VI.

EXAMPLE 3

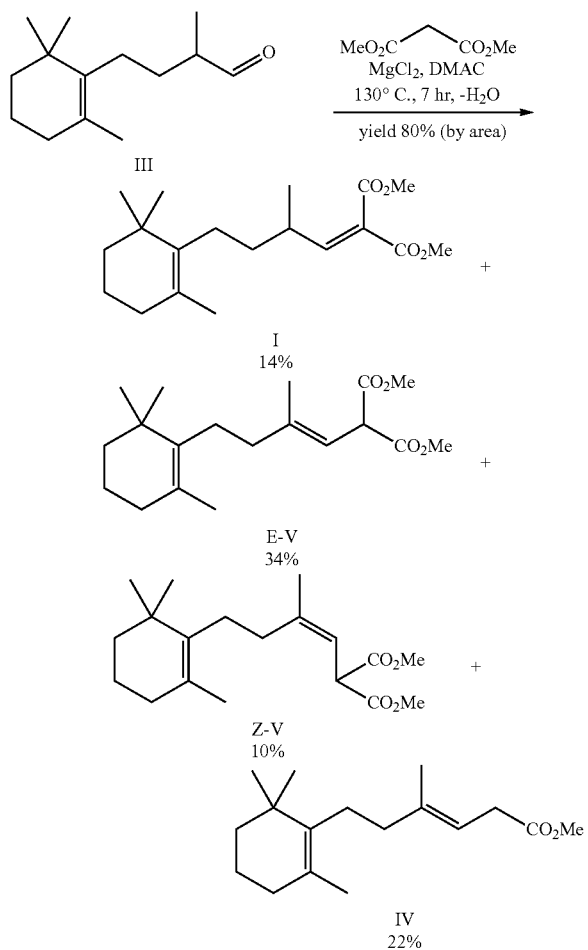

2-Methyl-4-(2,6,6-trimethylcyclohex-1-en-1-yl)butanal (Compound III, 2 g, 9 mmol, 96% purity), dimethyl malonate (2 g, 15.1 mmol), N,N-dimethylacetamide (2.4 g) and MgCl$_2$ (0.59 g, 6.2 mmol) were stirred at 130° C. for 7 hours. According to GC analysis, the reaction mixture contained 14% α,β-diester Compound I, 34% (E)-β,γ-diester Compound V, 10% (Z)-β,γ-diester Compound V, 22% (E)-β,γ-ester Compound IV and 1.1% unreacted Compound III.

EXAMPLE 4

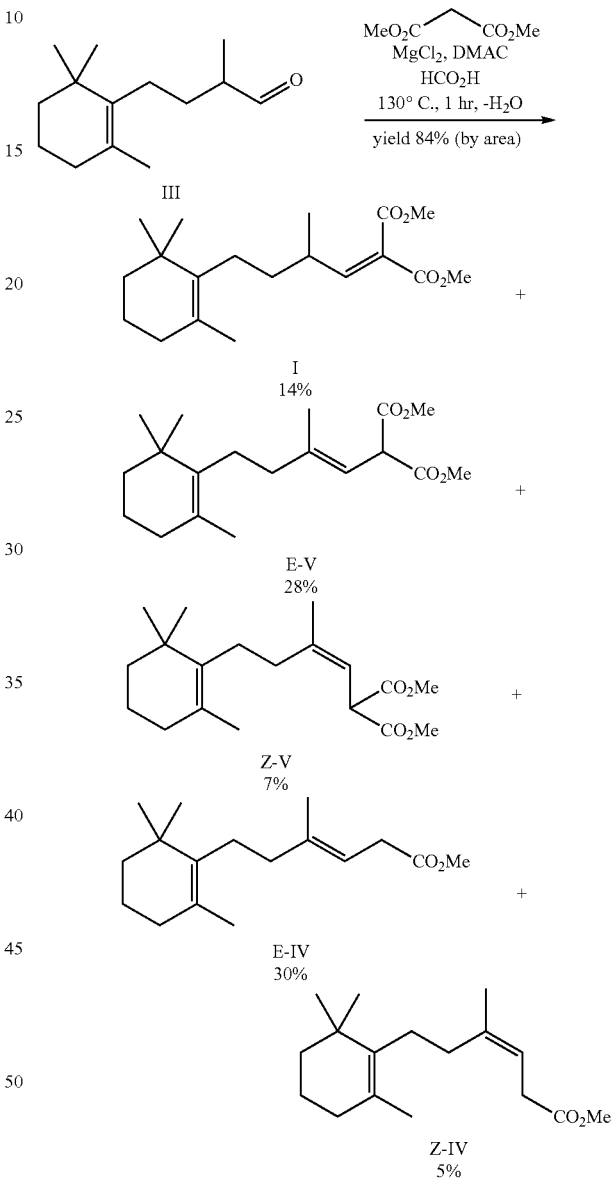

Following the same procedure described in Example 3 except that 0.2 g of anhydrous formic acid (4.3 mmol) was added to the reaction mixture. After 1 hour at 130° C., the starting material 2-methyl-4-(2,6,6-trimethylcyclohex-1-en-1-yl)butanal (Compound III) was completely consumed. According to GC analysis the reaction mixture contained 14% α,β-diester Compound I, 28% (E)-β,γ-diester Compound V, 7% (Z)-β,γ-diester Compound V, 30% (E)-β,γ-ester Compound IV and 5% (Z)-β,γ-ester Compound IV. The reaction was continued for additional 7 hours at 130° C. According to GC, the reaction mixture contained 12% (Z)-β,γ-ester Compound IV, 54% (E)-β,γ-ester Compound IV, 4% α,β-diester Compound I, 5% (Z)-β,γ-diester Compound V and 8% (E)-β,γ-diester Compound V.

EXAMPLE 5

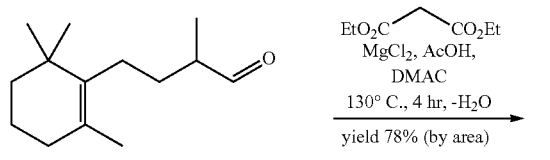

III

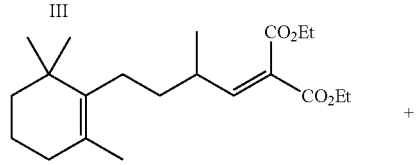

I
27%

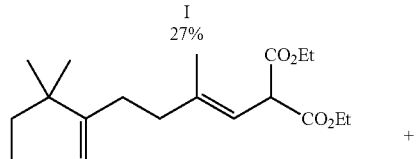

V
34%

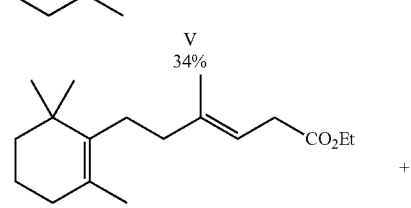

IV
17%

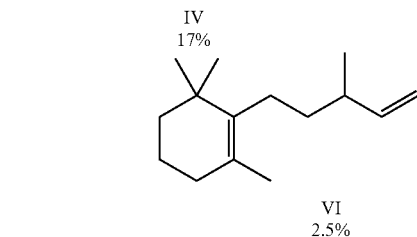

VI
2.5%

Acetic acid ("AcOH," 0.2 g, 3 mmol) was added to a mixture 2-Methyl-4-(2,6,6-trimethylcyclohex-1-en-1-yl)butanal (Compound III, 2 g, 9 mmol, 96% purity), N,N-dimethyl-acetamide (2.4 g), diethyl malonate (2.2 g, 13.7 mmol) and MgCl$_2$ (0.58 g, 6.1 mmol). The reaction mixture was stirred for 4 hours at 130° C. No Compound III was detected. According to GC analysis the mixture contained 27% α,β-diester Compound I, 34% trans-β,γ-diester Compound V, 17% (E)-β,γ-ester Compound IV and 2.4% conjugated α,β-ester Compound VI. The combined yield (based on % area in the GC spectrum) was 80.5%.

EXAMPLE 6

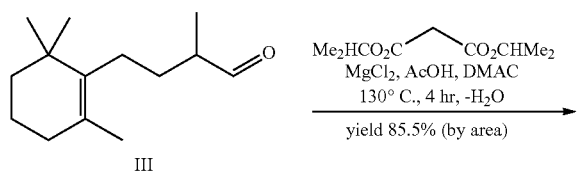

III

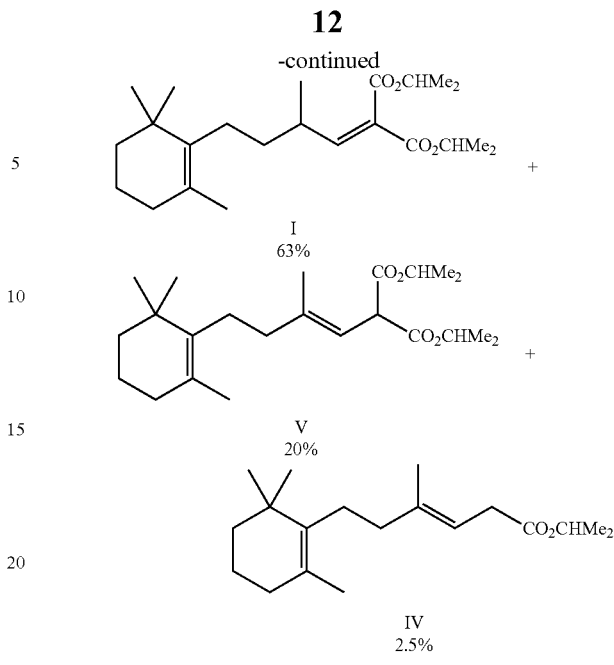

I
63%

V
20%

IV
2.5%

The reaction of 2-methyl-4-(2,6,6-trimethylcyclohex-1-en-1-yl)butanal (Compound III) with diisopropyl malonate and an equal mole amount of acetic acid following the procedure described in Example 5 required about 4 hours for complete conversion of Compound III. The reaction mixture contained according to GC analysis 63% α,β-diester Compound I, 20% (E)-β,γ-isomer Compound V, and 2.5% (E)-β,γ-ester Compound IV.

EXAMPLE 7

III

IV
62.2%

VI
19.9%

Acetic acid (0.6 g, 10 mmol) was added to a mixture of 2-methyl-4-(2,6,6-trimethylcyclohex-1-en-1-yl)butanal (Compound III, 2 g, 9 mmol, 96% purity), N,N-dimethyl-acetamide (2.4 g), diethyl malonate (2.2 g, 13.6 mmol) and MgCl$_2$ (0.58 g, 6.1 mmol). The reaction mixture was stirred for 6 hours at 180° C. According to GC analysis, the reaction mixture contained 62.2% (E)-β,γ-ester Compound IV and 19.9% α,β-ester Compound VI.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of preparing an unsaturated malonate, one skilled in the art can choose different aldehydes, dialkyl malonate, Lewis acid, carboxylic acid, solvent, reaction temperature, and/or reaction time. Further, the ratios among the reaction reagents can also be determined by a skilled artisan without undue experimentation.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A process for the preparation of an unsaturated malonate, or an isomer thereof, comprising the steps of:
performing a reaction between an aldehyde of formula A and a dialkyl malonate of formula B

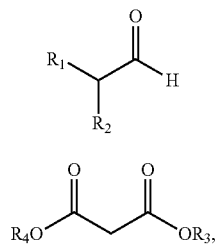

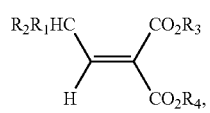

in which each of $R_1$, $R_2$, $R_3$ and $R_4$, independently, is selected from the group consisting of a straight or branched $C_1$-$C_{20}$ alkyl, straight or branched $C_2$-$C_{20}$ alkenyl, and straight or branched $C_2$-$C_{20}$ alkynyl;
wherein the reaction is performed in the presence of a Lewis acid; thereby forming a product containing an unsaturated malonate of formula C and the Lewis acid is magnesium chloride.

2. The process of claim 1, wherein the reaction is performed in the presence of an aprotic dipolar solvent.

3. The process of claim 1, wherein the reaction is performed in the presence of a carboxylic acid that is selected from the group consisting of formic acid, acetic acid, propionic acid, citric acid, and any combinations thereof.

4. The process of claim 2, wherein the aprotic dipolar solvent is selected from the group consisting of N,N-dimethylformamide (DMF), N,N-dimethylacetamide (DMAC), N-Methyl-2-pyrrolidone (NMP), dimethylsulfoxide (DMSO), and any combinations thereof.

5. The process of claim 1, wherein the reaction is performed at a temperature of 100 to 160 ° C. for at least 5 hours.

6. The process of claim 1, wherein the product further contains a compound of formula D, a compound of formula E, a compound of formula F, or any isomer thereof:

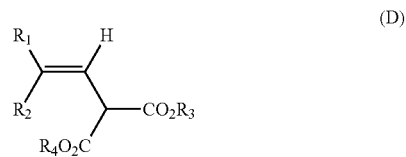

7. The process of claim 6, further comprising the step of converting the
compound of formula C or the compound of formula D under an alkoxydecarbonylating condition thereby forming a compound of formula E, a compound of formula F, or any isomer thereof.

8. The process of claim 1, wherein the aldehyde of formula A is Compound III of the following formula:

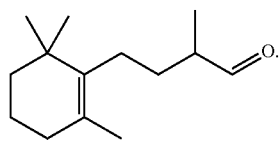

9. The process of claim 1, wherein the dialkyl malonate of formula B is dimethyl malonate or diethyl malonate.

10. The process of claim 1, wherein the product contains Compound I of the following formula:

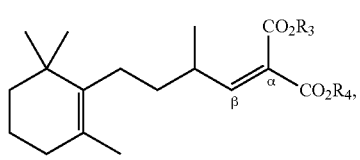

in which each of $R_3$ and $R_4$, independently, is methyl or ethyl.

11. The process of claim 1, wherein the product contains Compound IV of the following formula:

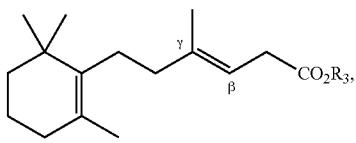

Compound V of the following formula:

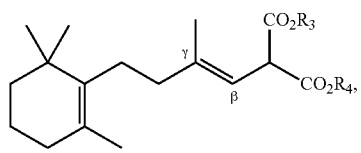

or a combination thereof, in which each of $R_3$ and $R_4$, independently, is methyl or ethyl.

12. The process of claim 11, further comprising the step of converting Compound I or V to Compound IV.

13. The process of claim 11, further comprising the step of converting Compound I, IV, or V to Compound II of the following formula:

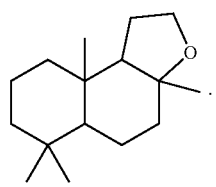

14. The process of claim 1, wherein the reaction is performed in a batch reactor or a continuous reactor, in which the continuous reactor is a single Continuous Stirred Tank Reactor (CSTR), multiple CSTRs in series, or a microreactor.

15. A process for the preparation of an unsaturated malonate, or an isomer thereof, comprising the steps of:
performing a reaction between an aldehyde of formula A and a dialkyl malonate of formula B

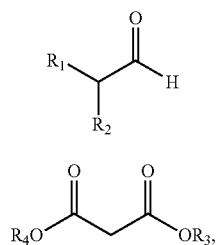

in which each of $R_1$, $R_2$, $R_3$ and $R_4$, independently, is selected from the group consisting of a straight or branched $C_1$-$C_{20}$ alkyl, straight or branched $C_2$-$C_{20}$ alkenyl, and straight or branched $C_2$-$C_{20}$ alkynyl; wherein the reaction is performed in the presence of a Lewis acid and a carboxylic acid; thereby forming a product containing an unsaturated malonate of formula C

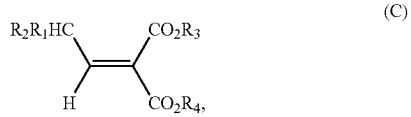

and the carboxylic acid is selected from the group consisting of formic acid, acetic acid, propionic acid, citric acid, and any combinations thereof.

16. The process of claim 15, wherein the reaction is performed in the presence of an aprotic dipolar solvent selected from the group consisting of N,N-dimethylformamide (DMF), N,N-dimethylacetamide (DMAC), N-Methyl-2-pyrrolidone (NMP), dimethylsulfoxide (DMSO), and any combinations thereof.

17. The process of claim 15, wherein the product contains Compound IV of the following formula:

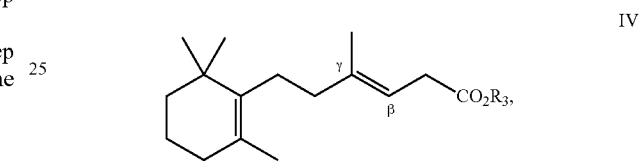

Compound V of the following formula:

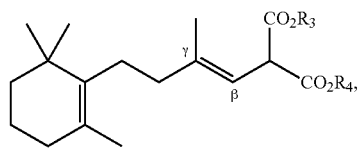

or a combination thereof, in which each of $R_3$ and $R_4$, independently, is methyl or ethyl; and Compound I, IV, or V is further converted to Compound II of the following formula:

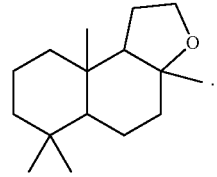

18. The process of claim 15, wherein the reaction is performed in a batch reactor or a continuous reactor, in which the continuous reactor is a single Continuous Stirred Tank Reactor (CSTR), multiple CSTRs in series, or a microreactor.

19. A process for the preparation of an unsaturated malonate, or an isomer thereof, comprising the steps of:
performing a reaction between an aldehyde of formula A and a dialkyl malonate of formula B (A)

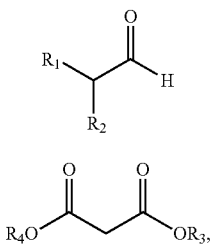

(B)

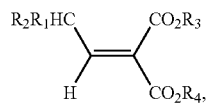

in which each of $R_1$, $R_2$, $R_3$ and $R_4$, independently, is selected from the group consisting of a straight or branched $C_1$-$C_{20}$ alkyl, straight or branched $C_2$-$C_{20}$ alkenyl, and straight or branched $C_2$-$C_{20}$ alkynyl;

wherein the reaction is performed in the presence of a Lewis acid and an aprotic dipolar solvent; thereby forming a product containing an unsaturated malonate of formula C (C)

R$_2$R$_1$HC, CO$_2$R$_3$, H, CO$_2$R$_4$, and the aprotic dipolar solvent is selected from the group consisting of N,N-dimethylformamide (DMF), N,N-dimethylacetamide (DMAC), N-Methyl-2-pyrrolidone (NMP), dimethylsulfoxide (DMSO), and any combinations thereof.

20. The process of claim 19, wherein the product contains Compound IV of the following formula:

IV

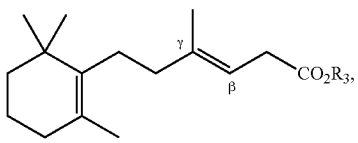

Compound V of the following formula.

V

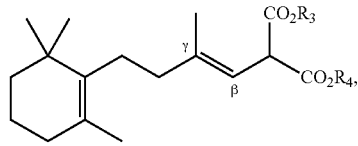

or a combination thereof, in which each of $R_3$ and $R_4$, independently, is methyl or ethyl; and Compound I, IV, or V is further converted to Compound II of the following formula:

II

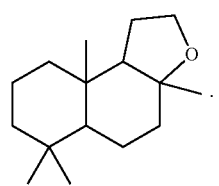

\* \* \* \* \*